US006617337B1

(12) United States Patent
Wilcox

(10) Patent No.: US 6,617,337 B1
(45) Date of Patent: *Sep. 9, 2003

(54) USE OF NITROXIDES FOR THE TREATMENT OF ESSENTIAL HYPERTENSION

(75) Inventor: Christopher S. Wilcox, Great Falls, VA (US)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/581,993

(22) PCT Filed: Sep. 21, 1998

(86) PCT No.: PCT/US98/19586

§ 371 (c)(1),
(2), (4) Date: Jan. 5, 2001

(87) PCT Pub. No.: WO99/13874

PCT Pub. Date: Mar. 25, 1999

Related U.S. Application Data

(63) Continuation of application No. 08/933,379, filed on Sep. 19, 1997, now Pat. No. 6,096,759.

(51) Int. Cl.[7] .................. A61K 31/445; A61K 31/44; A61K 31/42; A61K 31/40

(52) U.S. Cl. .................. 514/315; 514/345; 514/376; 514/424

(58) Field of Search .................. 514/315, 345, 514/376, 424

(56) References Cited

U.S. PATENT DOCUMENTS

| | | | |
|---|---|---|---|
| 4,046,901 A | 9/1977 | Nedelec et al. | 424/267 |
| 5,034,395 A | 7/1991 | Tamada et al. | 514/277 |
| 5,280,015 A * | 1/1994 | Jacobson et al. | 514/46 |
| 5,332,577 A | 7/1994 | Gertner et al. | 424/449 |
| 5,462,946 A | 10/1995 | Mitchell et al. | 514/315 |
| 5,516,881 A | 5/1996 | Lee et al. | 528/320 |
| 5,541,163 A | 7/1996 | Lavall ee et al. | 514/19 |
| 5,543,422 A | 8/1996 | Coutts et al. | 514/319 |
| 5,591,710 A | 1/1997 | Hsia | 514/6 |
| 5,622,994 A | 4/1997 | Carney et al. | 514/643 |
| 5,714,510 A * | 2/1998 | Proctor | 514/423 |
| 5,716,947 A * | 2/1998 | Proctor | 514/176 |
| 5,725,839 A | 3/1998 | Hsia | 424/9.33 |
| 5,741,893 A | 4/1998 | Hsia | 530/385 |
| 5,767,089 A | 6/1998 | Hsia | 514/21 |
| 5,804,561 A | 9/1998 | Hsia | 514/21 |
| 5,807,831 A | 9/1998 | Hsia | 514/21 |

FOREIGN PATENT DOCUMENTS

| WO | WO 92/22290 | 12/1992 |
|---|---|---|

OTHER PUBLICATIONS

CA116:75710, Murad, S. et al, Arch. Biochem. Biophys., 1992, 292(1), 234–8, abstract.*
Medline AN 96084808, Karmeli, F. et al, GUT, Sep. 1995, 37(3), 386–93, abstract.*
C.J. Bulpitt et al., Vitamin C and blood pressure, *J. Hypertens.* 8(12):1071–5 (1990).
D. Giugliano et al., Diabetes Mellitus, hypertension, and cardiovascular disease: which role for oxidative stress?, *Metabolism* 44(3):363–8 (1995).
S. Grunfeld et al., Role of Superoxide in the depressed nitric oxide production by the endothelium of genetically hypertensive rats, *Hypertension* 26(6 Pt 1): 854–7 (1995).
R.J. Gryglewski et al., Superoxide anion is involved in the breakdown of endothelium—derived vascular relaxing factor, *Nature* 320(6061): 454–6 (1986).
D.G. Harrison et al., Physiologic consequences of increased vascular oxidant stresses in hypercholesterolemia and atherosclerosis: implications for impaired vasomotion, *Am J. Cardiol* 75(6): 75B–81B (1995).
V.V. Khramtsov et al., In vitro and in vivo studies of the derivatives of 1,2–diazetine and nitronylnitroxide as donors and acceptors of nitric oxide. *Biokhimiya*, 61(10): 1731–1742 (1996). abstract.
K.V. Kumar et al. Are free radicals involved in the pathobiology of human essential hypertension?, *Ree Radic Res Commun.* 19(1): 59–66 (1993).
J. M. McCord, Oxygen–derived free radicals in postischemic tissue injury, *N. Engl. J. Med.* 312(3): 159–63 (1985).
Y. Miyamoto et al., "Potentiation of nitric oxide–mediated vasorelaxation by xanthine oxidase inhibitors," *Proc. Soc. Exp. Biol. Med.* 312(4): 366–373 (1996).
K. Nakazono et al., Does superoxide underlie the pathogenesis of hypertension? *Proc. Natl. Acad. Sci. USA* 88: 10045–10048 (1991).
G.M. Rubanyi et al., Superoxide anions and hyperoxia inactivate endothelium–derived relaxing factor. *Am. J. Physiol.* 250: H822–H827 (1986).
C.G. Schnackenberg et al. Normalization of blood pressure and renal vascular resistance in SHR with a membrane–permeable superoxide dismutase mimetic. *Hypertension*, 32(1): 59–64 (1998).
C.G. Schnackenberg et al., Long–term tempol administration attenuates the hypertension and production of 8–iso prostaglandin F2a in SHR. *Hypertension* 32(3): 622 (1998).

(List continued on next page.)

Primary Examiner—Rebecca Cook
(74) *Attorney, Agent, or Firm*—Morgan, Lewis & Bockius LLP

(57) ABSTRACT

The present invention encompasses methods of treating patients for essential hypertension. The invention also includes related pharmaceutical compositions of nitroxides. Specific drugs, such as 4-hydroxy-2,2,6,6-tetramethyl-1-piperidinyloxy (Tempol) are disclosed. These compositions are also contemplated for use in the treatment of oxidative stress and modulation of blood pressure.

22 Claims, 4 Drawing Sheets

OTHER PUBLICATIONS

H. Suzuki et al., In vivo evidence for microvascular oxidative stress in spontaneously hypertensive rats. Hydroethidine microfluorography. *Hypertension* 25(5): 1083–1089 (1995).

M.R. Tschudi et al., Direct in situ measurement of nitric oxide in mesenteric arteries. Increased decomposition by superoxide in hypertension. *Hypertension* 27(1): 32–35 (1996).

W.Y. Tse et al., Antioxidant status in controlled and uncontrolled hypertension and its relationship to endothelial damage. *J. Hum. Hypertens*. 89: 843–849 (1994).

M. Yoshioka et al., Effects of ascorbic acid on blood pressure and ascorbic acid metabolism in spontaneously hypertensive rats (SH Rats). *Internat. J. Vit. Nutr. Res.* 55: 301–307 (1985).

Tal, Neuroreport (1996) 7(8) 1382–84.

Karmeli et al. (1996) GUT 38(6) 826–31.

Monte et al. (1996) Free Radical Biol. Med. 21(4) 463–70.

Wilcox (2000) New Endothelium–Derived Metabolites of Arachidonic Acid that Mediate Vasodilation. Lewis K. Dahl Memorial Lecture, American Heart Association.

\* cited by examiner

US 6,617,337 B1

USE OF NITROXIDES FOR THE TREATMENT OF ESSENTIAL HYPERTENSION

This is a 371 of PCT/US/98/19586 filed Sep. 21, 1998 which is a continuation of 08/933,379 filed Sep. 19, 1997 now U.S. Pat. No. 6,096,759.

The work leading to this invention was partially funded by the United States Government under NIH grants DK 36079 and DK 49870.

FIELD OF THE INVENTION

This invention relates to the treatment of essential hypertension by administration of anti-hypertensive effective amounts of nitroxides, such as 4-hydroxy-2,2,6,6-tetramethyl-1-piperidinyloxy (Tempol or TMPN).

BACKGROUND OF THE INVENTION

Systemic hypertension is the most prevalent cardiovascular disorder in the United States, affecting more than 50 million individuals. Accordingly, efforts to prevent, diagnose and treat hypertension remain an important concern of national health care. Although major advances have been made as to public awareness of the importance of hypertension, introducing antihypertensive therapies and in controlling hypertension, the adverse metabolic effects of some classes of antihypertensive drugs and the disappointing results in preventing associated coronary disease have challenged the traditional approaches of treating the antihypertensive patient.

Essential Hypertension

Essential hypertension represents a collection of genetically based diseases and/or syndromes with a number of underlying inherited biochemical abnormalities which have yet to be elucidated. Hypertension leads to atherosclerosis and other forms of vascular pathology by damaging the endothelium. Endothelial damage produces a cascade of changes. Additionally, non-atherosclerotic hypertension-induced vascular damage can lead to stroke and end-stage renal disease. The measurement of blood pressure (BP) is one of the major methods of diagnosing essential hypertension. However, blood pressure is just one factor that is taken into account in the choice of therapy and drug selection for the treatment of the complex pathology which is essential hypertension.

Reactive Oxygen Species

Reactive oxygen species (ROS), such as superoxide anions ($O_2^-$), hydroxyl radicals, and hydrogen peroxide ($H_2O_2$) have been implicated in atherosclerosis, diabetes, ischemia-reperfusion injury and hypertension (Giugliano et al., 1995 *Metab.* 44: 363–368; Harrison et al., 1995 *Am. J. Cardiol.* 75: 75B–81B; McCord et al., 1985 312: 159–163; and Kitiyakara et dl., *Curr. Opin. Nephrol Hypertens.* In press). Compared to normotensive individuals, hypertensive patients have higher plasma hydrogen peroxide, superoxide anion and lipid peroxides while having lower levels of the antioxidant, ascorbic acid (Lacy et al., 1998 *J. Hypertens.* 16: 291–303; Kumar et al., 1993 *Free Rad. Res. Commun.* 19: 59–66; Tse et al., 1994 *J. Hum. Hypertens.* 89: 843–849; Bulpitt et al., *J. Hypertens.* 8: 1071–1075). However, the molecular mechanism for oxygen toxicity in vascular diseases, such as essential hypertension, remains to be elucidated.

Enzymes such as superoxide disumutase (SOD) catalyze the dismutation of superoxide radicals to remove the radicals from the subject's system where the radicals can destroy tissue. Experiments in which SOD was administered to rats did not reduce blood pressure in either normal rats or in spontaneously hypersensitive rats (SHR). However, an SOD fusion protein and oxypurinol, an inhibitor of xanthine oxidase, when administered separately have decreased blood pressure in SHR, but not normal rats (Nakazono et al., 1991 *Proc. Nat'l Acad. Sci. USA* 88: 10045–10048). Other short term studies of ROS inhibition have indicated that blood pressure can be reduced in the SHR animal model (Yoshioka et al., 1985 *Int. J. Vitam. Nutri. Res.* 55: 301–307; Nakazono et al., 1991 *Proc. Natl Acad. Sci. USA* 88: 10045–10048; Suzuki et al., 1998 *Proc. Natl Acad. Sci. USA* 95: 47544759; Susuki et al., 1995 *Hypertens.* 25: 1083–1089). Another antioxidant, ascorbic acid, has also lowered the blood pressure level in the SHR animal model. However, the SHR model has also indicated abnormalities in ascorbic acid metabolism (Yoshioka et al., 1985 *Internat. J. Vit. Nutr. Res.* 55: 301–307). This evidence indicates that superoxide radicals in and around vascular endothelial cells play roles in the pathogenesis of hypertension in the SHR model.

Nitric oxide (NO), also known as endothelium-derived relaxing factor (EDRF), is synthesized by nitric oxide synthase (NOS) in many types of cells including vascular endothelial cells, vascular smooth muscle cells, activated macrophages, neuronal cells and glial cells (Miyamoto et al., 1996 *Proc. Soc. Exp. Biol. Med.* 211: 366–373). Gryglewski et al., (1986 *Nature* 320: 454–456) showed that $O_2^-$ reacts with NO to form the potentially toxic molecular species, peroxynitrite ($ONOO^-$), which can effectively deplete NO in vascular endothelial cells. Rubanyi et al., (1986) demonstrated that $O_2^-$ inactivates EDRF in coronary artery rings (*Am. J. Physiol.* 250: H822–H827.) Scavenging of $O_2^-$ enhances endothelium-dependent vasodilation and increases NO release from mesenteri arterioles (Tschudi et al., 1996 *Hypertens.* 27: 32–35) and endothelial cells (Grunfeld et al., 1995 *Hypertens.* 26: 854–857) in SHR. However, the complete mechanism for the vasodilatory actions of $O_2^-$ scavengers has yet to be elucidated. Specifically, although in vitro evidence exists suggesting that $O_2^-$ contributes to increased systemic vascular tone in the SHR, the role of $O_2^-$ in increased renal vascular resistance (RVR) and baseline mean arterial pressure (MAP) of SHR in vivo remains unclear (Schnackenberg et al., 1998 *Hypertens.* 32: 59–64).

There are many other examples in which severe oxidative stress is found without hypertension. These include, for examples, poisoning with carbon tetrachloride, diabetes mellitus and hypercholesteremia. Indeed, the evidence for oxidative stress in these conditions is better than in hypertension. Therefore, the finding that correction of oxidative stress also reduced blood pressure is not predictable (Kitiyakara et al., in press).

Nitroxides

Nitroxides have been used in ameliorating the deleterious effects of toxic oxygen-related species such as $O_2^-$ (see Mitchell et al., 1995 U.S. Pat. No. 5,462,946; Hsia 1997 and 1998 U.S. Pat. Nos., 5,591,710; 5,725,839; 5,741,893; 5,767,089; 5,804,561; and 5,807,831; and Lee et al., 1996 U.S. Pat. No. 5,516,881). Some nitroxides, such as Tempol (4-hydroxy-2,2,6,6-tetramethyl-1-piperidinyloxy), have been indicated for use in treating renal hypertension disorders (Carney et al., 1997 U.S. Pat. No. 5,622,994; WO 92/22290). However, renal hypertension occurs as a result of reduced blood flow to the kidney and is not essential hypertension.

SUMMARY OF THE INVENTION

The treatment of essential hypertension has long presented a serious problem to the medical profession. This invention proposes a new method of treating essential hypertension in a subject, such as a human, using compositions containing nitroxides. The nitroxides contemplated for use in the treatment of essential hypertension include nitroxides selected from the group consisting of TEMPO, DOXYL or PROXYL nitroxides. One preferred nitroxide is 4-hydroxy-2,2,6,6-tetramethyl-1-piperidinyloxy (Tempol).

This invention also contemplates a method of treating a patient with essential hypertension comprising the step of administering a blood pressure lowering amount of a nitroxide, preferably in admixture with a pharmaceutically acceptable carrier and/or an excipient. This method utilizes the same nitroxides and methods of administration as described above.

Methods of administering pharmaceutical compositions containing nitroxides for treatment of essential hypertension include oral, transdermal, parenteral and intravenous routes of administration.

This invention also provides for a method of treating essential hypertension comprising the steps of administering to a subject, such as a human, any of the above pharmaceutical compositions in combination with a second antihypertensive agent (e.g., benzothiadiazine diuretics, loop diuretics, potassium-sparing diuretics, sympatholytic agents, angiotensin-converting enzyme inhibitors, calcium channel blocking agents, direct vasodilators, as well as other antioxidants).

The invention likewise provides ranges of disclosed agents such as Tempol to be administered to a subject for the treatment of essential hypertension. The pharmaceutical compositions of Tempol to be administered to a subject include an intravenous dose of from about 0.07 mg/kg/hr to about 750 mg/kg/hr; an intravenous bolus dose of from about 0.025 mg/kg/day to about 400 mg/kg/day; and an oral dose from about 0.05 mg/kg/day to about 1,000 mg/kg/day.

This invention also contemplates simultaneously treating essential hypertensive and oxidative stress comprising the step of administering a pharmaceutical composition comprising an effective amount of a nitroxide, such as Tempol. Such composition could further comprise additional antihypertensives and/or No providing agents.

DESCRIPTION OF THE INVENTION

Figure 1:
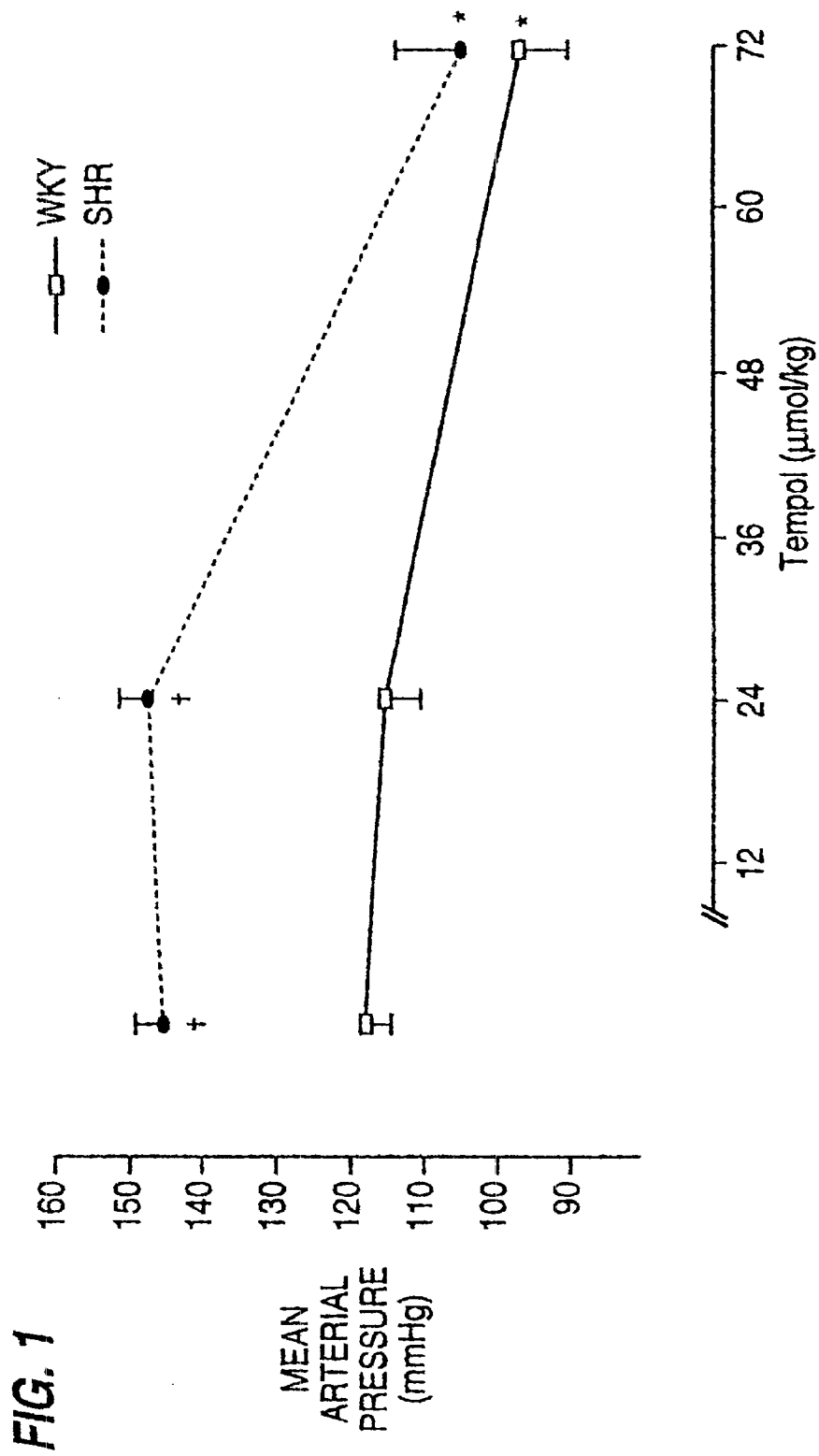
FIG. 1. MAP during baseline conditions (Basal) and during bolus injection of Tempol (24 and 72 $\mu$mol/kg i.v.) in anesthetized WKY (□, =6) and SHR (●, n=6). * P<0.05 vs. Basal; †P<0.05 vs. WKY.

Providing novel effective methods of treating essential hypertension is greatly needed by the millions who suffer from the disease. This invention provides a method of controlling essential hypertension by administration of a nitroxide by itself in combination with another antihypertensive agent or antioxidants.

1. Definitions

By "essential hypertension" is meant essential primary or idiopathic hypertension which is a systemic hypertension of an unknown cause. Essential hypertension is the cause of 95% of all cases of hypertension diagnosed. It includes hypertension of all grades, including borderline, mild moderate and severe. It also includes hypertensive urgencies and emergencies or hypertensive crises, and indeed all cases of hypertension where there is not a known cause. Secondary hypertension is systemic hypertension of a known and reversible cause. Secondary causes are largely those due to renal or renal artery diseases or endocrine disorders. These account for fewer than 2–10% of the diagnosed cases of hypertension.

By "blood pressure lowering amount" is meant that amount of a compound that produces a therapeutically effective concentration significantly decreasing the blood pressure of a subject. A clinically significant reduction of BP would be a fall in BP of greater than 5% relative to either the patient's normal base line BP or the patient's BPs under placebo therapy.

By "effective concentration of Tempol" or "effective concentration of a nitroxide" is meant that concentration of Tempol or nitroxide which significantly lowers the blood pressure of the hypertensive subject. In a human subject, normal diastolic blood pressure (BP) is considered to be normal when on two visits to the physician the diastolic BP is below 90 mm Hg or the systolic blood pressure on two visits to the physician is below 140 mm Hg. In certain circumstances, such as patients with heavy proteinuria or diabetic nephropathy, a lower goal for BP of 120–125 (systolic) and 70–75 (diastolic) mm Hg is considered optimal currently. The definitions, goals of therapy, and uses of conventional anti-hypertensive agents have recently been summarized in a consensus document published by the National Institutes of Health entitled the Sixth Report of the Joint Commission on the Detection, Evaluation and Treatment of Hypertension (National Institutes of Health, National Heart, Lung and Blood Institute, 1998).

The "nitroxide compounds," which may be useful in the present invention, will be structurally diverse because the requisite property of the nitroxides is their ability to mimic superoxide dismutase (SOD) and catalase activity via the nitroxide free radical. The main requirement of the nitroxide compound is the presence of a stable free radical. Therefore, the nitroxides described in this invention include stable nitroxide free radicals, their precursors, and their derivatives in a heterocyclic or linear structure, as represented by the general formula:

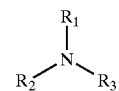

where $R_1$ and $R_2$ combine together with the nitrogen to form a heterocyclic group; and wherein the atoms in the heterocyclic group may be all carbon atoms, or may be carbon atoms as well as one or more N, O, and/or S atoms (such as, but not limited to a pyrrole, imidazole, oxazole, thiazole, pyrazole, 3-pyrroline, pyrrolidine, pyridine, pyrimidine, or purine, or derivatives thereof). The heterocyclic group is preferably a 5-membered ring (such as PROXYL, or pyrroline) or a 6-membered ring (such as piperidinyl or TEMPO), with substitution at the carbon alpha to the nitrogen by electron-donating groups, which may include straight or branched chain alkyl or aryl groups, preferably methyl or ethyl groups, although other longer carbon chain species could be used.

In a more preferred embodiment, the TEMPO, DOXYL or PROXYL nitroxides or their derivatives may be used, as shown below:

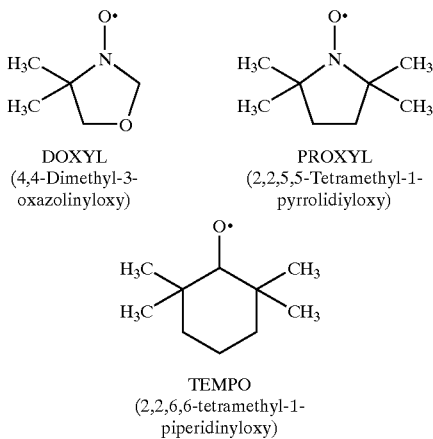

DOXYL
(4,4-Dimethyl-3-oxazolinyloxy)

PROXYL
(2,2,5,5-Tetramethyl-1-pyrrolidiyloxy)

TEMPO
(2,2,6,6-tetramethyl-1-piperidinyloxy)

The TEMPO, DOXYL or PROXYL nitroxides may or may not be substituted at any atom, other than the nitrogen bearing the oxygen free radical, with any combination of at least one of the following substituents: acetamido, aminomethyl, benzoyl, 2-bromoacetamido, 2-(2-(2-bromoacetamido)ethoxy)ethylcarbamoyl, carbamoyl, carboxy, cyano, 5-(dimethylamino)-1-naphthalenesulfonamido, ethoxyfluorophosphinyloxy, ethyl, 5-fluoro-2, 4-dinitroanilino, hydroxy, 2-iodoacetamido, isothiocyanato, isothiocyanatomethyl, methyl, maleimido, maleimidoethyl, 2-(2-maleimidoethoxy)ethylcarbamoyl, maleimidomethyl, maleimido, oxo, and phosphonooxy. The TEMPO, DOXYL or PROXYL nitroxides may also be substituents on, for example, 17β-hydroxy-5α-androstane, decane, nonadecane, 5α-cholestane, stearic acid. In the alternative, the TEMPO, DOXYL or PROXYL nitroxides may form the methyl, ethyl, or propyl ester with stearic acid. Additional nitroxides that are within the scope of the present invention are discussed in U.S. Pat. Nos. 5,462,946 and 5,591,710, which are herein incorporated by reference.

The most preferred embodiment of the invention for the treatment of essential hypertension are the nitroxides, 4-hydroxy-2,2,6,6-tetramethyl-1-piperidinyloxy (Tempol) or less preferred, 2,2,6,6-tetramethyl-1-piperidinyloxy (TEMPO).

The compounds of the invention include nitroxide compounds that can be administered via either the oral, parenteral or topical routes and other routes of administration known to those skilled in the art. In general, these compounds are most desirably administered in the dosages discussed in Example 2, although variations will necessarily occur depending upon the weight, age, and condition of the subject being treated and the presence of co-morbid conditions that may affect the pharmokokinetics or pharmokodynamics of the agents. These will vary according to the particular route of administration chosen. Other variations may also occur depending upon the species of animal being treated and its individual response to said medicament, as well as on the type of pharmaceutical formulation chosen, and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day or via sustained release formulations, or by continuous administration by intravenous infusion or dermal application. For example, tablets may be uncoated or they may be coated by known techniques to delay disintegration and absorption in the gastrointestinal tract thereby providing a sustained action over a longer period. Potential time delayed materials include glyceryl monostearate or glyceryl distearate. They may also be coated by the techniques described in U.S. Pat. Nos. 4,256,108; 4,166,452; and 4,265,874 to form osmotic therapeutic tablets for control release.

The compounds of the invention may be administered alone or in combination with pharmaceutically acceptable carriers of diluents by any of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (e.g., preferably corn, potato or tapioca starch), alginic acid and certain complex silicates, together with granulation binders such as polyvinylpyrrolidone, sucrose, gelatin, and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar, as well as high molecular weight polyethylene glycols.

When aqueous suspensions and/or elixirs are desired for oral administration, the active ingredient may be combined with various sweetening or flavoring agents, coloring matters or dyes, and, if so desired, emulsifying and/or suspending agents as well, together with such diluents as water, ethanol, propylene glycol, glycerin and various like combinations thereof. Aqueous suspensions may also contain the active materials in admixture with excipients suitable for aqueous suspensions. Useful suspending agents include, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, lecithin or condensation products of an alkylene oxide with fatty acids (e.g., polyoxyethylene stearate), or condensation products of ethylene oxide with long chain aliphatic alcohols (e.g. heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyoxyethylene sorbitan monooleate). The aqueous suspensions may also contain one or more preservatives (e.g., ethyl or n-propyl p-hydroxybenzoate).

For parenteral administration, solutions of a therapeutic compound of the present invention could be formulated as a ready to use solution in an isotonic vehicle of normal saline containing suitable stabilizers. The active agent may also be formulated as a dry, sterile powder or as a lyophilized powder which would require reconstitution with an acceptable isotonic, sterile liquid. These aqueous solutions are suitable for intravenous, intramuscular, or subcutaneous injection purposes. The preparation of all these solutions under sterile conditions is readily accomplished by standard pharmaceutical techniques well known to those skilled in the art. These preparation can also be used in combination with other antihypertensive agents such as diuretics.

Any of the above methods of administering the active ingredients (e.g. nitroxides) is contemplated to treat subjects suffering from essential hypertension (also known as primary or idiopathic hypertension). It is contemplated to use these agents in patients with all grades of hypertension from borderline to severe, in patients with accelerated or malignant hypertension, and in those patients with hypertensive urgencies, emergencies or crises. In treating higher grades of hypertension or those categories outlined above, the combination of anti-hypertensive and free radical scavenging properties may be especially beneficial. Intracellular- and extracellular-oxidative stress is hypothesized to be a critical link between hypertension and the atherosclerotic complications of vascular disease that lead to myocardial infarction, stroke and peripheral vascular disease. Thus, therapy directed simultaneously at hypertensive and intracellular and extracellular oxidative stress mediated by oxygen radicals ($O_2^-$) and other reactive oxygen species (ROS) is highly attractive. The compounds and formulations containing these compounds are also considered for use to lower blood pressure and to reduce oxidative stress. These compounds should be utilized in combination with lifestyle modifications (e.g., weight reduction, alcohol restriction, exercise, restricting dietary sodium intake, supplementing dietary calcium and potassium and magnesium intake, special diets, caffeine restriction and smoking cessation) and other strategies to combat oxidative stress (for example, vitamin E and C, selenium, chromium) and general measures to improve oxygen homeostasis so as to limit ongoing oxygen radical production (e.g., vasodilator therapy, appropriate use of nitric oxide and NO donors) to further prevent complications arising from hypertension and oxidative stress.

The pharmaceutically acceptable composition comprising nitroxides can further be combined with other antihypertensive agents. Antihypertensive agents include benzothiadiazine diuretics (e.g., thiazides, phthalimidines and quinazolines), loop diuretics (e.g., furosemide, ethacrynic acid and bumetanide), potassium-sparing diuretics (e.g., spironolactone, triamterene and amiloride), sympatholytic agents (e.g., centrally acting agents such as methyldopa; β-adrenergic blocking agents such as propranolol; α-adrenergic blocking agents such as prazosin; mixed α- and β-adrenergic blocking agents such as labetalol; ganglion blocking agents such as mecamylamine; and peripherally acting sympatholytic agents such as guanethidine), angiotensin-converting enzyme inhibitors (e.g., captopril, enalapril, lisinopril, quinapril, ramipril, benazepril, fosinopril, spiropril, perindopril, and moexipril), calcium channel blockers (e.g., nifedipine, etc.), and direct vasodilators (e.g., sodium nitroprusside, hydralazine and minoxidil). For additional active agents to be used in combination with nitroxides, see CECIL TEXTBOOK OF MEDICINE 264–265 (20th ed., J. C. Bennett and F. Plum editors, W. B. Saunders Co., Philadelphia 1996).

Other pharmaceutical compositions include combinations of a nitroxide and an NO providing reagent (e.g., NO generating agents and NO donors). Preferred NO providing agents include: sodium nitroprusside (Nipride), S-nitrosoacetylpenacillamine (SNAP), 3-morpholino-synonimin-hydrochloride (SIN-1), 3-morpholino-N-athoxycarbonyl-sydnonimin (molsidomin), amyl nitrite (isoamyl nitrite), nitroglycerin (glyceryl trinitrite), isosorbide dinitrate (Isodil), isosorbide-5-mononitrite (Imur), and erythrityl tetranitrate (cardilate). Other agents which are NO generating or are NO donors could also be utilized in combination with nitroxides such as Tempol to treat essential hypertension and oxidative stress.

To evaluate the recent finding that an absent TGF response to NOS blockade in the salt-restricted Sprague-Dawley rat could be restored by local microperfusion of L-arginine into the JGA, several studies were performed. As a part of the study, defective NO action in the JGA of SHR was assessed from the TGF response to microperfusion of the low molecular weight nitroxide, 4-hydroxy-2,2,6,6-tetramethyl-1-piperidinyloxy (Tempol). Tempol is a nonmetal, cell membrane-permeable superoxide dismutase (SOD) mimetic that can protect against cardiac reperfusion damage or cardiomyocyte oxidative damage (Iannone et al, 1989 Biochem. Pharm. 38: 2581–2586; Nilsson et al., 1989 J. Biol. Chem. 19: 11131–11135). Tempol has been demonstrated to be a stable spin trap for $O_2^-$ and to reduce $O_2^-$ related injury resulting from ischemia/reperfusion, inflammation and radiation (Goffinan et al., 1992 Radiat. Oncol. Biol. Phys. 22: 803–806; Hahn et al, 1992 Cancer Res. 52: 1750–1753; and Mitchell et al., 1991 Arch. Biochem. Biophys. 289: 62–70).

The following working examples which disclose methods of administering nitroxide compositions therefore, specifically point out preferred embodiments of the present invention. These examples are not to be construed as limiting in any way the scope of the invention. Other examples using other formulations containing nitroxides alone or in combination with one or more antihypertensive agents and/or antioxidants will be apparent to one skilled in the art. Assays analogous to those described below can be utilized in examining the efficacy of these formulations for the treatment of essential hypertension.

EXAMPLE 1

Materials and Methods. Studies were undertaken on male SHR and WKY, weighing 235–300 g, and maintained on a standard rat chow (Purina Rat Chow, St. Louis, Mo.) with a sodium content of 0.3 g·100 $g^{-1}$. They were allowed free access to food and water until the day of study.

Series 1: RT-PCR analysis of mRNA abundance of ecNOS and bNOS transcripts in glomeruli or renal cortex of SHR and WKY. As the amount of NOS may play a role in hypertension, especially in the SHR model, these studies were designed to test the hypothesis that transcripts for constitutive NOS were diminished in the cortex of the SHR as compared to WKY rats. bNOS transcripts and protein are expressed abundantly in the macula densa of the renal cortex, and previous studies have shown a close correlation between bNOS mRNA transcript abundance in renal cortex and bNOS transcript abundance in isolated macula densas. Accordingly, studies of bNOS mRNA expression were undertaken in outer cortical tissue with the assumption that differences likely reflect changes predominantly in macula densa bNOS mRNA. Endothelial cell NOS (ecNOS) mRNA is more widely expressed in the vasculature, and therefore its abundance was assessed in individual glomeruli that were microdissected from outer cortical nephrons.

Under thiobarbital anesthesia (pentobarbital 100 mg·$kg^{-1}$ i.p.), the abdomen was opened and the aorta cannulated to allow flushing of the kidneys with ice-cold dissection solution. This fluid contained 135 mM NaCl, 1 mM $Na_2HPO_4$, at pH 7.4. For isolation of outer cortical kidney RNA, one kidney from 6 SHR and one from 6 WKY was cut longitudinally, and a segment of outer cortex removed and digested with collagenase (1%) for 30 min at 37° C. Glomeruli were dissected under a stereomicroscope in rinse solution at 4° C. This contained (200 µl volume): 170 µl dissection solution, 20 µl of 5 µM DTT, 10 µl of 10 mM vanadyl ribonucleoside complex. Dissected glomeruli were further cleaned in buffer under stereomicroscope at 4° C. This contained (200 µl volume): 170 µl dissection solution, 20 µl of 5 µM of DTT, and 10 mM of 2 U/µl RNA sin+. Finally, glomeruli were transferred to centrifuge tubes containing lysis solution. The lysis solution contained (200 µl volume): 166 µl deionized water, 4 µl of 2% Triton X-100, 20 µl of 5 mM DTT, and 10 µl of 2 U/µl RNA sin+. Total RNA was extracted using RNA ATAT-60™ (Tel-test B, Inc., Friendswood, Tex.). The mRNA was reverse transcribed (RT) with Oligo $(dT)_{16}$ as primer and MuLV reverse transcriptase using an RNA PCR Kit (Perkin Elmer, Inc., Branchburg, N.J.).

The primers used for PCR of the bNOS gene product were those described previously. For bNOS, the sense primer was: 5'-GTCGAATTCCGAATACCAGCCTGATCCATGGAA-3'(Seq. #1), and the antisense primer was 5'-CGCGGATCCCATGCGGTGGACTCCCTCCTGGA-3' (Seq. #2). The predicted product had a length of 599 base pairs. β-actin was selected as a "housekeeper gene" for comparison. The primers used for β-actin mRNA were: sense primer 5'-GATCAAGATCATTGCTCCTC-3'(Seq. #3) and antisense primer: 5'-TGTACAATCAAAGTCCTCAG-3'(Seq. #4). The PCR product had a predicted length of 426 bp. The amounts of NOS cDNAs were normalized by the amounts of β-actin cDNA. The reaction mixture contained 50 pmol of each primer, 1.25 mM deoxynucleotide mixture, 2.5 µl Taq DNA polymerase, 10 mM Tris-HCl (pH 10), 50 mM KCl, 1.5 MM $MgCl_2$, 0.001% (w/v) gelatin in a final volume of 50 µl. PCR was carried out as follows: after an initial melting temperature of 94° C. for 4 min, there was 30 sec of denaturation at 94° C.; 45 sec of annealing at 60° C.; and 45 sec of extension at 72° C. for repeated cycles of amplification, followed by a final extension at 72° C. for 7 min. The PCR products were analyzed on a 1.5% agarose gel stained with ethidium bromide and visualized under UV light. The size of the products were compared to a rat kidney cDNA probe for bNOS. To verify the authenticity of the PCR products, the amplified bNOS cDNAs from the rat kidney cortex of an SHR and WKY rat were purified by MICROCON™ (Amicon Co., Beverly, Mass.) and sequenced with an AmliTaq cycle sequencing kit (Perkin Elmer, Inc., Branchburg, N.J.).

Transcript abundance for ecNOS was assessed in single outer cortical glomeruli, isolated using the method of Pelayo et al. (1994) *Am. J. Physiol.* 267: F497–F503. Separate groups of SHR (n=6) and WKY (n=6) were prepared as described above. For these studies, mRNA abundance was examined per single glomerulus. After anesthesia and preparation of the animal, blue 1–5 µm latex microspheres (Polysciences, Warrington, Pa.) were infused in HEPES buffer (pH 7.4) into the left kidney. After perfusion, the kidney was excised, cut into coronal slices, placed on ice, and a glomerulus from the outer cortex microdissected under stereomicroscopy. Thereafter, the mRNA was extracted, reverse transcribed, and amplified as described above. The primers used for ecNOS were: sense primer 5'-GTCGAATTCCTGGCGGCGGAAGAGAAGGA-GC-3'(Seq. #5) and antisense: 5'-CGC-GGATCCGGGGCTGGGTGGGGAGGTGATGTC-3' (Seq. #6). The predicted product had a length of 691 base pairs and was compared to a rat kidney cDNA probe for ecNOS from our laboratory.

Care was taken to optimize conditions for the RT-PCR. For each study, parallel analyses were undertaken of serially diluted amounts of cDNA to ensure that product (as assessed by densitometry) increased log-linearly with cDNA amount in the ranges used. Negative controls were undertaken by PCR without prior RT, and by RT-PCR of the buffer used.

Series 2: Comparison of ecNOS, bNOS, and iNOS protein expression in kidneys of SHR and WKY. These studies in WKY and SHR rats were undertaken to assess the hypothesis that changes in renal cortical gene transcript abundance were accompanied by changes in NOS gene translation products. Six SHR and six WKY rats were anesthetized, and their kidneys prepared as described above. Slices of kidney outer cortex were dissected and homogenized on ice in 1 ml buffer containing 20 mm Tris pH 7.2, 0.5 mM EDTA, 0.5 mM EGTA, 1 mM leupeptin, 1 mM DDT, 0.1 mM phenylmethylsulfonyl fluoride using a Potter-Elvehjem Teflon glass tissue homogenizer. Homogenates were sonicated three times for 40 sec, centrifuged at 12,000 g for 15 min, and diluted in sodium dodecyl sulfate (SDS) buffer (0.5 M TRIS-HCl pH 6.8, 20% (v/v) glycerol, 4.6% (w/v) SDS). A sample was prepared to contain 350 µg protein and was applied to an 8% SDS gel. Proteins were separated by SDS-PAGE and electroblotting to a nitrocellulose membrane (Pierce, Rockford, Ill.) that was stained by Ponceau solution to ascertain that protein transfer to the membrane was complete. The nitrocellulose membranes were incubated with 3% nonfat dry milk in Tris-buffered saline with 0.1% Tween-20 (TBST) for 1 h, followed by overnight incubation with a mouse monoclonal antibody for bNOS, iNOS, or ecNOS in a 1:400 dilution. After rinsing in TBST, membranes were incubated for 1 h with anti-mouse IgG antibody conjugated horseradish peroxidase at a 1:1000 dilution. Membranes were then rinsed with TBST, and bNOS, iNOS, or ecNOS protein was detected by diaminobenzidine (DAB) with 0.3% hydrogen peroxide.

Series 3: Immunohistochemical study of ecNOS and bNOS distribution in the kidney of SHR and WKY. These studies were undertaken to assess the distribution of ecNOS immunoreactivity in vascular and glomerular capillary endothelium and bNOS in macula densa cell cytoplasm in SHR and WKY rats. Specifically, differences in constitutive and inducible NOS expression in various tissues could also indicate the role of NOS in hypertension. After anesthesia, the abdominal aorta of 5 SHR and 5 WKY was cannulated and the kidneys perfused with 0.154 M NaCl followed by paraformaldehyde lysine periodate (PLP) solution for 5 min, cut into slices, and immersed into PLP overnight at 4° C. before embedding in wax (polyethylene glycol 400 distearate; Polysciences, Inc., Warrington, Pa.) or paraffin.

Two µm wax sections were processed for light microscopic immunohistochemistry using the streptavidin-biotin-horseradish peroxidase complex technique (LSAB kit, Dako, Calif.). Briefly, sections were dewaxed, rehydrated, and incubated with 3% $H_2O_2$ for 10 min to eliminate endogenous peroxidase activity. After rinsing in Tris-buffered saline with 0.1% Tween 20 (TBST), sections were treated with blocking serum for 10 min and incubated with primary mouse monoclonal antibody in a dilution of 1:100 for bNOS and ecNOS (both from Transduction Laboratories Inc., Lexington, Ky.) for 1 h. After rinsing with TBST, the sections were incubated with the secondary antibody, biotinylated rabbit polyclonal antibody against mouse immunoglobin (Dako, Denmark), in a dilution of 1:600 for 30 min, rinsed, and incubated for 20 min with horseradish peroxidase (HRP) labeled streptavidin. After rinsing with TBST, HRP was detected by diaminobenzidine (DAB) with hydrogen peroxide. The sections were counter stained with hematoxylin and examined under light microscopy.

For electron-microscopic (EM) immunocytochemistry using the post-embedding immunogold procedure, one mm$^3$ blocks of kidney cortex was dehydrated and embedded in Lowicryl. Ultrathin sections were cut on an ultramicrotome, mounted on colloidin-coated nickel grids, and processed for immunogold labeling. The sections were incubated with 0.1 M NH$_4$Cl for 1 h, rinsed with buffer solution (0.02 M Tris HCl, 0.15 M NaCl, 0.05% Tween 20, adjusted to pH 7.2) for 15 min, and incubated with mouse monoclonal antibody against ecNOS (Transduction Laboratories Inc., Lexington, Ky.) at a concentration of 1:100 overnight at 4° C. After three 10-min buffer washes, 30 nm gold-labeled goat anti-mouse IgG secondary antibody (Amersham Life Science, Buckinghamshire, U.K.) was applied for 2 h at a dilution of 1:50. Thereafter, the sections were washed with buffer, incubated with 2% glutaraldehyde/PBS solution for 30 min, rinsed with distilled water, counter stained with uranyl acetate and lead citrate, and examined with an electron microscope (Hitachi 7000 transmission electron microscope). In order to evaluate semi-quantitatively the degree of ecNOS immunogold labeling, a blinded observer assessed EM pictures of sections from 3 SHR and 3 WKY rats. The number of immunogold particles detected overlying epithelial cells were counted and expressed as the number of particles/μm of glomerular basement membrane.

Series 4. Effects of inhibition of bNOS on maximal TGF responses in SHR and WKY. These experiments further examined the SHR hypertension model and whether the enhanced TGF of the SHR kidney is due to a blunted generation of NO by bNOS in the macula densa or whether NOS inhibition is diminished in the SHR model. Groups of SHR and age-matched WKY rats were prepared for in vivo micropuncture, microperfusion, and TGF studies as described in detail previously. In brief, animals were anesthetized with thiobarbital (Inactin, 100 mg·kg$^{-1}$; Research Biochemicals, Inc., Natick, Mass.). A catheter was placed in a jugular vein for fluid infusion and in a femoral artery for recording of mean arterial pressure (MAP) from the electrically damped output of a pressure transducer (Statham, Inc.). A tracheotomy tube was inserted and the animals were allowed to breathe spontaneously. The left kidney was exposed by a flank incision, cleaned of connective tissue, and stabilized in a Lucite cup. This kidney was bathed in 0.154 M NaCl maintained at 37° C. After completion of surgery, rats were infused with a solution of 0.154 M NaCl and 1% albumin at 1.5 ml·h$^{-1}$ to maintain a euvolemic state. Micropuncture studies were begun after 60 min for stabilization.

For orthograde microperfusion of the loop of Henle (LH), a micropipette (8 μm OD) containing artificial tubular fluid (ATF) stained with FD&C dye was inserted into a late proximal tubule. Injections of the colored ATF identified the nephron and the direction of flow. An immobile bone wax block was inserted into this micropuncture site via a micropipette (10–15 μm) and connected to a hydraulic drive (Trent Wells, Inc., LaJolla, Calif.) to halt tubular fluid flow. A perfusion micropipette (6–8 μm) containing ATF and test compounds or vehicle was inserted into the proximal tubule downstream from the wax block and connected to a nanoliter perfusion pump (WPI, Sarasota, Fla.). A pressure micropipette (1–2 μm) was inserted into the proximal tubule upstream from the wax block to measure proximal stop flow pressure (PSF). Changes in PSF are an index of changes in glomerular capillary hydraulic pressure ($P_{GC}$). Measurements of PSF were made in each nephron during zero loop perfusion and during perfusion with ATF at 40 nl·min$^{-1}$, which produces a maximal TGF response, defined as the difference between PSF values recorded during perfusion of the loop with ATF at 0 and 40 nl·min$^{-1}$.

The maximal TGF responses were determined in SHR (n=4) and WKY rats (n=4) to perfusion of the LH with ATF+vehicle and contrasted with the maximal TGF responses during perfusion with ATF+7-nitroindazole (7-NI; 10$^{-4}$ M).

Series 5: Maximal TGF responses during microperfusion of L-arginine in SHR and WKY. L-arginine had previously been shown not to lower blood pressure or the glomerular filtration rate in the SHR model. However, L-arginine can restore a TGF response to NOS blockade in tested rats adapted to low salt intake. Therefore, the role of L-arginine was tested in the SHR model. This series examined the effect of a reduced delivery of L-arginine to the macula densa on NO generation, as assessed in Series 4. Groups of SHR (n=4) and WKY rats (n=3) were prepared for microperfusion. PSF was recorded during orthograde LH perfusion at 0 and 40 nl·min$^{-1}$ with ATF+vehicle and ATF+L-arginine (10$^{-3}$ M). (Previous studies had shown that this was a maximally effective dose.)

Series 6: Effects on maximal TGF responses of microperfusion of Tempol into the JGA of SHR and WKY. The purpose of this example was to determine whether oxygen-derived free-radicals in the JGA potentiate TGF in the SHR, and whether this effect can be modulated by the nitroxide, Tempol. Groups of SHR (n=5) and WKY rats (n=5) were prepared for studies of retrograde microperfusion into the macula densa. As anticipated from its high membrane permeability, Tempol had rather inconsistent results when perfused orthogradely from the late proximal tubule. Therefore, these studies of TGF were conducted with retrograde microperfusion from the early distal (ED) tubule into the macula densa. After identifying the nephron with FD&C green, the last proximal convolution was vented and a wax block placed upstream. A micropipette (8–10 μm OD) was inserted into the ED tubule upstream from an oil droplet. The loop of Henle was perfused retrogradely with perfusate entering the macula densa segment directly at 0 and 20 nl·min$^{-1}$. This represents a maximal activation for TGF by retrograde perfusion. Preliminary studies indicated that a dose of Tempol of 10$^{-3}$ M was maximally effective, and the effects were reversible. Therefore, this dose was used thereafter in the test animals (Dosage/kg would usually be lower in larger animals). Comparisons were made of maximum TGF responses obtained during perfusion of ATF+vehicle (ethanol) and ATF+Tempol.

Statistical Methods. Values are reported as mean±SEM. An analysis of variance (ANOVA) was applied to the within-group data for SHR and WKY; where appropriate, post hoc Dunnett's t tests were applied thereafter. Values were taken as statistically significant at p<0.05.

Results. For Series 1, ecNOS mRNA abundance was consistently greater in outer cortical glomeruli from SHR than WKY, although similar densities were apparent for β-actin mRNA. This was confirmed by densitometric analysis. The cDNA obtained from one glomerulus was analyzed and found to correspond fully with the published sequence for rat ecNOS.

RT-PCR products corresponding to cDNAs for bNOS were obtained from outer cortex of 6 SHR and 6 WKY rat kidneys. The density of the bands obtained from SHR was consistently greater than that for WKY, although similar densities were apparent for β-actin. This difference was confirmed by densitometric analysis. Analysis of the PCR product from one kidney confirmed that it corresponded fully to the published sequence for rat bNOS.

For Series 2, Western analysis of proteins extracted from the outer cortex of kidneys of SHR and WKY rats demonstrated bands of immunoreactivity corresponding to iNOS and bNOS. A band for ecNOS was not consistently detected in the cortex. The expression of bNOS and iNOS immunoreactive proteins were increased 50–65% in the cortex of the SHR compared to the WKY.

For Series 3, the distribution of ecNOS and bNOS immunoreactivity in the kidney cortex of SHR and WKY corresponded to previously published data in Sprague-Dawley rats. The ecNOS immunoreactivity was readily demonstrable in the endothelium of arcuate arteries in the renal cortex of WKY and SHR. In WKY, immunoreactivity was of a relatively modest intensity, whereas in SHR the immunoreactivity in the endothelium appeared more dense. Immunostaining for ecNOS was also apparent in endothelium of outer cortical arterioles, where it appeared to be less dense in WKY than in SHR. Using EM immunocytochemistry to assess ecNOS immunoreactive expression in glomerular capillary endothelium more quantitatively, the number of immunogold particles along the capillary walls of outer cortical glomeruli was significantly greater in SHR than WKY (SHR: $0.51\pm0.05$, n=41 vs. WKY: $0.32\pm0.05$, n=40, gold particles·$\mu m^{-1}$; $p<0.01$). Examination of bNOS immunoreactivity showed heavy staining of the macula densa cell plaque. There appeared to be less prominent stain in WKY compared to SHR. Kidneys from 5 SHR and 5 WKY rats were tested systematically for immunocytochemical staining. The results showed clearly stronger macula densa staining for bNOS in SHR compared to WKY in each pair examined by a blinded observer.

The baseline data for the micropuncture/microperfusion studies of rats of Series 4–6 are shown in Table 1. It is apparent that compared to WKY, SHR rats were of similar body and kidney weight but had consistently higher levels of blood pressure and slightly greater heart rates. Tubuloglomerular feedback (TGF) parameters showed consistently higher values for proximal stop flow pressure during perfusion of the loop of Henle at 0 and 40 nl·min$^{-1}$ and a greater maximal TGF response, as assessed from differences between PSF during perfusion at 0 and 40 nl·min$^{-1}$ in SHR, which averaged 135% of the WKY control.

For Series 4, maximum TGF responses were contrasted in SHR and WKY rats during addition of vehicle or 7-NI to orthograde LH perfusates. As shown in Table 2, the maximum TGF responses were greater in SHR than WKY during perfusion of ATF+vehicle. The addition of 7-NI increased maximal TGF responses consistently in WKY by an average of 39%, but had no significant effects on TGF responses of SHR.

For Series 5, TGF responses were contrasted in SHR and WKY during addition of L-arginine to orthograde LH perfusates. As shown in Table 3, the maximum TGF responses were greater in SHR compared to WKY during perfusion of ATF+vehicle. Addition of L-arginine significantly blunted ATF responses of WKY by an average of 18% but had no significant effects on TGF responses of SHR.

For Series 6, TGF responses were contrasted in SHR and WKY during addition of the membrane-permeable nitroxide SOD mimetic, Tempol, to LH perfusates. As shown in Table 4, maximum TGF responses were again greater in SHR than in WKY during retrograde perfusion of ATF+vehicle. Addition of Tempol ($10^{-3}$ M) to the retrograde perfusions of ATF blunted TGF responses in SHR and WKY rats significantly. However, the blunting of TGF was significantly ($p<0.01$) greater in the SHR rats than in WKY rats. When normalized to the initial response, the percentage reduction in TGF with Tempol was again greater in SHR (SHR: $-26\pm2$ vs. WKY: $-17\pm3\%$; $p<0.05$).

Two additional microperfusion studies were undertaken to assess the mechanism of Tempol action in SHR. In the first, local microperfusion of Tempol ($10^{-4}$ M) in artificial plasma via the efferent arteriole into peritubular capillaries was undertaken in 6 rats. A dose of $10^{-6}$ M 5-nitroacetylpenacillamine (SNAP), a NO donor compound, was microperfused into the macula densa of the rats. The dose was just subthreshold, but during Tempol microperfusion the SNAP significantly ($p<0.01$) blunted TGF response by more than 25%. This demonstrates synergistic interaction between Tempol and a NO donor compound, such as SNAP. Other NO donor compounds include nitroprusside and nitrates.

In the other study, Tempol ($10^{-4}$ M artificial plasma) was microperfused into efferent arterioles of 7 SHR rats for 4–10 min periods. Whereas before Tempol administration there was no significant TGF response to microperfusion of the NOS inhibitor 7-nitroindazole (7-NI) into the macula densa at the $10^{-4}$ M concentration, during Tempol microperfusion there was a robust increase in TGF in the presence of 7-NI of greater than 25%. This increase in TGF with 7-NI during Tempol administration is similar to the increase observed with 7-NI in WKY rats. Therefore, Tempol had normalized the response to NOS blockage in the hypertensive model. This also implies that it had normalized the action of NO in this setting, thereby correcting the defect in the NO action in hypertension and restoring normal vascular control. This is filly consistent with its action on a free radical scavenging agent that thereby protects NO from radical attack.

In view of the findings from the examples, it is seen that the expression of both constitutive and inducible NOS isoforms are increased in the SHR kidney, and that the increase in constitutive NOS isoforms in the cortex and JGA appears to be transcriptionally regulated since it is accompanied by an increase in mRNA abundance. Despite this evidence of enhanced NOS expression in the JGA and/or the renal cortex, the TGF responses of SHR are exaggerated and are unresponsive either to local blockade of nNOS by microperfusion of 7-NI into macula densa or to local provision of NOS substrate by microperfusion of L-arginine into the macula densa. These enhanced responses persist after normalization of the renal perfusion pressure with a suprarenal aortic clamp and therefore are not a direct consequence of the elevated BP.

The results with the relatively bNOS-selective antagonist 7-NI, show that it has no effect on TGF responses of SHR despite potentiating TGF responses of WKY. Thus, the functional response to NOS inhibition is diminished in the SHR.

TABLE 1

Whole animal and kidney weights, mean arterial pressure (MAP), heart rate (HR), and tubuloglomerular feedback parameters in WKY and SHR rats used for functional studies

| Rat strain | No. of rats | No. of nephrons | Body weight (g) | Kidney weight (g) | MAP (mm Hg) | HR (min$^{-1}$) | PSF (mm Hg) during LH perfusion (nl · min$^{-1}$) at: 0 | 40 | 0–40 |
|---|---|---|---|---|---|---|---|---|---|
| WKY | 10 | 23 | 268 ± 8 | 1.17 ± 0.04 | 116 ± 3 | 354 ± 6 | 36.3 ± 0.5 | 28.0 ± 0.4 | 8.4 ± 0.3 |
| SHR | 13 | 32 | 266 ± 15 | 1.04 ± 0.06 | 158 ± 4 | 378 ± 8 | 41.0 ± 0.5 | 29.8 ± 0.4 | 11.2 ± 0.4 |
| p value | | | ns | ns | <0.001 | <0.05 | <0.001 | <0.01 | <0.001 |

Mean ± SEM values from rats of series 4–6. PSF, proximal stop flow pressure.

TABLE 2

Values of proximal stop flow pressure (PSF) as a function of rate of orthograde perfusion of artificial tubular fluid (ATF) in SHR and WKY: Effects of 7-nitroindazole (7-NI) or renal perfusion pressure

| Rat strain | Added to ATF | No. of rats | No. of nephrons | MAP (mm Hg) | PSF (mm Hg) during retrograde LH perfusion (nl · min$^{-1}$) at: 0 | 40 | 0–40 |
|---|---|---|---|---|---|---|---|
| WKY | Veh | 4 | 8 | 121 ± 5 | 37.9 ± 0.8 | 28.4 ± 0.9 | 9.5 ± 0.5 |
|  | 7-NI | 4 | 8 |  | 38.1 ± 0.8 | 25.0 ± 1.2 | 13.2 ± 0.7 |
| p value |  |  |  |  | ns | <0.05 | <0.001 |
| SHR | Veh | 4 | 13 | 168 ± 11 | 41.3 ± 0.9 | 29.6 ± 0.6 | 11.8 ± 07 |
|  | 7-NI | 4 | 13 |  | 41.0 ± 1.0 | 29.3 ± 0.7 | 12.5 ± 0.6 |

Mean ± SEM values from series 4. Veh, vehicle; MAP, mean arterial pressure.

TABLE 3

Values of proximal stop flow pressure (PSF) as a function of rate of orthograde perfusion of artificial tubular fluid (ATF) in SHR and WKY: Effects of L-arginine

| Rat strain | Added to ATF | No. of rats | No. of nephrons | PSF (mm Hg) during LH perfusion (nl · min$^{-1}$) at: 0 | 40 | 0–40 |
|---|---|---|---|---|---|---|
| WKY | Veh | 3 | 9 | 36.1 ± 0.7 | 28.4 ± 0.6 | 7.7 ± 0.8 |
|  | L-arginine | 3 | 9 | 36.1 ± 0.7 | 29.8 ± 0.5 | 6.3 ± 0.4 |
| p value |  |  |  | ns | ns | <0.05 |
| SHR | Veh | 4 | 9 | 41.1 ± 1.2 | 30.2 ± 1.1 | 10.4 ± 0.7 |
|  | L-arginine | 4 | 9 | 41.0 ± 1.2 | 30.4 ± 0.7 | 10.6 ± 0.7 |
| p value |  |  |  | ns | ns | ns |

Mean ± SEM values. Veh, vehicle.

TABLE 4

Values of proximal stop flow pressure (PSF) as a function of rate of retrograde perfusion of artificial tubular fluid (ATF) in SHR and WKY: Effects of the nitroxide, superoxide dismutase mimetic, Tempol

| Rat strain | Added to ATF | No. of rats | No. of nephrons | PSF (mm Hg) during LH perfusion (nl · min$^{-1}$) at: 0 | 40 | 0–40 |
|---|---|---|---|---|---|---|
| WKY | Veh | 5 | 10 | 34.9 ± 0.8 | 26.7 ± 0.7 | 8.1 ± 0.4 |
|  | Tempol | 5 | 10 | 34.7 ± 0.8 | 28.0 ± 0.9 | 6.7 ± 0.4 |
| p value |  |  |  | ns | ns | <0.05 |
| SHR | Veh | 5 | 10 | 40.3 ± 0.8 | 28.8 ± 0.6 | 11.5 ± 0.6 |
|  | Tempol | 5 | 10 | 40.8 ± 0.8 | 32.1 ± 0.9 | 8.5 ± 0.8 |
| p value |  |  |  | ns | <0.05 | <0.001 |

Mean ± SEM values. Veh, vehicle.

Conclusion. Microperfusion of L-arginine into the JGA blunted maximal TGF responses in WKY, yet did not significantly modify responses in SHR. This implies that L-arginine delivery was not limiting for NO generation in the JGA of the SHR. This is consistent with previous findings that L-arginine does not lower BP or improve the glomerular filtration rate (GFR) of the SHR. The present findings indicate that a deficient delivery of L-arginine to the JGA cannot explain the enhanced TGF of outer cortical nephrons of SHR.

Tempol is a low molecular weight, nontoxic compound that equilibrates rapidly between extra- and intracellular compartments, thereby conferring much greater protection against post-ischemic cellular damage than SOD. Unlike other SOD mimetics, it is not dependent on metals and therefore is stable in the intracellular environment that contains high $Mg^{+2}$ concentrations.

Because endothelium-dependent vasodilatation is impaired in the SHR, in vitro studies were done in view of the SHR to further evaluate the effect of Tempol on renal vasoconstriction, vasodilatation and hypertension.

In the first group, the short-term actions of Tempol were determined in anesthetized rats. Baseline mean arterial pressure (MAP) and renal vascular resistance (RVS) were significantly elevated in the SHR (n=6) compared to the WKY (n=6). The following data was obtained:

MAP: SHR=145±4 vs. WKY=118±3 mm Hg,

RVR: SHR=32±4 vs. WKY=10±8 mm Hg/ml/min.

Tempol was administered intravenously at 4 mg/kg and the animals tested

MAP: SHR=108±8 vs. WKY=98±6 mm Hg

RVR: SHR=17±2 vs. WKY=15±1 mm Hg/ml/min

Tempol 12 mg/kg was given intravenously:

MAP: SHR=80±5 vs. WKY=99±7 mm Hg

The longer term effect of administration of Tempol at the rate of 250 mg/kg/day given intraperitoneally for 7 days, showed no effect on the MAP in WKY rats, but decreased MAP in the SHR (p<0.01) from 133±2 to 120±3 mm Hg.

EXAMPLE 2

The finding that Tempol is an effective treatment in the model of genetically-transmitted essential hypertension suggests that Tempol and its derivative forms, as well as other nitroxides, can be used to treat essential hypertension in humans. Tempol and other nitroxides have the special potential advantage of not only treating hypertension, but also correcting intra- and extra-cellular oxidative stress simultaneously.

The following compositions are suggestions only and are not meant to limit the scope of the invention. Oral compositions may contain fillers and, additionally, preservatives along with other inert or active agents.

A. Compositions for Oral Administration 500 mg Tempol 500 mg starch 5 mg magnesium stearate.

The composition may be placed in capsules which may be enteric coated. Other preparations can include concentrations of Tempol from about 1 mg/kg/day to about 500 mg/kg/day. In rats, effective dosages administered orally include from about 0.7 to about 15,000 mg/kg/day orally, or more preferred from about 0.7 to about 1,500 mg/kg/day orally, or most preferred from about 7 to about 150 mg/kg/day. In humans, because of the slower metabolism, the effective dosages of Tempol administered orally include from about 0.07 to about 7,500 mg/kg/day orally, or more preferred from about 0.07 to about 750 mg/kg/day orally, or most preferred from about 0.7 to about 75 mg/kg/day.

B. Compositions for Parenteral Administration

From about 1 gram of Tempol is added to from about 50 to about 100 mls of 5% dextrose or normal saline or other suitable isotonic solution for intravenous (i.v.) administration. Additional compositions contemplated for parenteral use include from about 0.5 mM to about 100 mM Tempol. More preferred would be about 0.5 mM to about 10 mM Tempol administered in an isotonic vehicle intravenously (i.v.).

Tempol may be administered on a solid support. One example of a solid support are patches. Patches for the administration of Tempol can be formulated as adhesive patches containing a nitroxide. For example, the patch may be a discoid in which a pressure-sensitive silicone adhesive matrix containing the active agent may be covered with a non-permeable backing. The discoid may either contain the active agent in the adhesive or may have attached thereto a support made of material such as polyurethane foam or gauze that will hold the active agent (e.g., Tempol). Before use, the material containing the active agent would be covered to protect the patch.

C. Compositions for Intravenous Administration

In rats, effective dosages administered intravenously (i.v.) include: (1) from about 0.25 to about 800 mg/kg by i.v. bolus dosing, more preferred from about 0.25 to about 80 mg/kg by i.v. bolus dosing, and most preferred from about 2.5 mg/kg to about 8 mg/kg by i.v. bolus dosing; and (2) from about 0.5 to about 2,000 mg/kg/hr by i.v. infusion, more preferred from about 0.5 to about 200 mg/kg/hour by i.v. infusion, and most preferred from about 5 to about 20 mg/kg/hour by i.v. infusion. In humans, because of the slower metabolism, the effective dosages of Tempol administered intravenously include: (1) from about 0.025 to about 400 mg/kg by i.v. bolus dosing, more preferred from about 0.025 to about 40 mg/kg by i.v. bolus dosing, and most preferred from about 0.25 mg/kg to about 4 mg/kg by i.v. bolus dosing; and (2) from about 0.05 to about 1,000 mg/kg/hr by i.v. infusion, more preferred from about 0.05 to about 100 mg/kg/hour by i.v. infusion, and most preferred from about 0.5 to about 10 mg/kg/hour by i.v. infusion.

D. Compositions for Dermal Administration

A patch or other solid support composed of trilaminate of an adhesive matrix sandwiched between a non-permeable backing and a protective covering layer is prepared in the following manner:

Two grams of Tempol is applied to from about 5 grams of a pressure-sensitive silicone adhesive composition BIOPSA™ Q7-2920 (Dow Corning Corp., Midland, Mich., U.S.A.). The adhesive is applied to a polyester film to provide in successive layers to provide about 200 mg of active agent per $cm^2$. The film containing the adhesive is then made into a patch of 10 $cm^2$. The patch is covered with a protective layer to be removed before application of the patch.

Patches may be prepared containing permeation enhancers such as cyclodextrin, butylated hydroxyanisole, or butylated hydroxytoluene. However, it should be remembered that the active agents of this invention are effective on application to the epidermal tissue. When the patches are to be applied to thin or abraded skin, there is little need to add a permeation enhancer.

EXAMPLE 3

Materials and Methods. In Examples 3 to 6, groups of male SHR and WKY rats (200 to 300 g) were maintained on tap water and standard chow (Harlan-Teklad Inc.). In Example 3, renal hemodynamics and MAP during bolus intravenous injection of Tempol were compared in anesthetized SHR and WKY. In order to do this experiment, WKY (n=6) and SHR (n=6) were anesthetized with thiobutabarbital (100 mg/kg i.p., Inactin, Research Biochemicals International) and maintained at 37° C. on a servocontrolled heated rodent operating table. A tracheostomy was performed with polyethylene PE-240 tubing, and the left jugular vein and carotid artery were cannulated with PE-50 tubing. Intravenous infusion of 1% albumin dissolved in 0.154 M NaCl solution was infused at 2 mL/h i.v. to maintain an euvolemic state. A midline incision was made, and the left renal artery was isolated. A blood-flow probe was placed around the renal artery and connected to a transit-time blood flowmeter (1RB, Transonic Systems Inc.). We have previously shown that this method of measuring real-time changes in RBF is valid in the rat (Welch et al., 1995 *Am. J. Physiol.* 37: F175–F178).

MAP was continuously recorded from the carotid artery using a Statham pressure transducer (model P23, Gould Instruments) and MACLab data acquisition program. After 60 minutes of equilibration, there was a basal period for measurement of MAP and RBF over 30 minutes. Then the MAP and RBF responses to Tempol at 24 and 72 μmol/kg i.v. were determined.

Statistics. All values shown are mean±SE. ANOVA was used to determine statistical significance in groups 1 and 2. Student's t test was used to determine significance in groups 3 and 4, where the comparison was limited to two observatims. P<0.05 was considered statistically significant. The statistical methods used are the same for Examples 3 to 6.

Results. FIG. 1 shows the MAP during baseline conditions and after intravenous injections of Tempol at 24 and 72 μmol/kg in WKY and SHR. Baseline MAP was significantly elevated in SHR compared with WKY (145±4 versus 118±3 mm Hg, respectively; P<0.05). Low-dose Tempol (24 μmol/kg IV) had no effect in either the WKY (114±5 mm Hg) or SHR (147±4 mm Hg). However, higher-dose Tempol normalized the MAP of the SHR to the level of WKY. Tempol (72 μmol/kg IV) significantly (P<0.05) decreased MAP by 11% in WKY (96±6 mm Hg) and by 28% in SHR (104±9 mm Hg).

Renal hemodynamics were studied during basal conditions and infusion of Tempol at 24 and 72 μmol/kg in WKY and SHR. Baseline RBF was similar between groups (WKY, 7.1±0.7; SHR, 6.8±1.0 mL/min) and was not affected during Tempol (WKY, 6.6±0.7; SHR, 6.7±0.8 mL/min). In contrast, baseline RVR was significantly increased in SHR compared with WKY (24±3 versus 17±1 mm Hg·mL$^{-1}$·min$^{-1}$, respectively; P<0.05). Low-dose Tempol had no effect on RVR in either group (WKY, 17±1; SHR, 24±3 mm Hg·mL$^{-1}$·min$^{-1}$). However, higher-dose Tempol normalized the RVR of the SHR to the level of WKY. Tempol at 72 μmol/kg significantly (P<0.05) decreased RVR by 29% in SHR (17±2 mm Hg·mL$^{-1}$·min$^{-1}$), while having a minimal effect in WKY (15±1 mm Hg·mL$^{-1}$·min$^{-1}$).

Previous studies investigating the short-term actions of $O_2^-$ on blood pressure in SHR demonstrated that bolus injection of a xanthine oxidase inhibitor to block the formation of $O_2^-$ from xanthine or CuZn SOD acutely decreased MAP in the SHR; however, results for WKY were not reported (Miyamoto et al., 1996; Nakazono et al, 1991 Proc. Nat'l Acad. Sci. USA 88: 10045–10048). This treatment corrects $O_2^-$ generation only from xanthine oxidase, whereas the proposed mechanism of action of Tempol as a SOD mimetic predicts that it should correct $O_2^-$ overproduction from all sources. Moreover, it can gain access to both intra- and extra-cellular sites, and will therefore correct oxidative stress arising intra- or extra-cellularly. Most other antioxidants, such as vitamin C and SOD act purely extracellularly. Therefore, we compared the effect of scavenging $O_2^-$ on MAP in SHR to their genetic control WKY. We show that acute Tempol administration normalized MAP and RVR in SHR to the level of WKY.

Earlier studies have established a role for $O_2^-$ in the aorta and mesenteric arterioles of SHR (Auch-Schwelk et al., 1989 Hypertens. 13: 859–864; Miyamoto et al., 1996; Grunfeld et al., 1995; and Susuki et al., 1995 Hypertens. 25: 1083–1089). However, the kidneys play an important role in the development and maintenance of hypertension. Tempol vasodilated the renal vasculature in SHR more than in WKY. Under control conditions, RVR was significantly elevated in SHR, and Tempol normalized RVR in SHR to the level of WKY. Because Tempol reduced MAP without changing RBF, renal vasodilation was inferred. The RVR response to Tempol may be a result of RBF autoregulation. Whether Tempol directly or indirectly decreases RVR in SHR remains to be further elucidated. This is the first demonstration that the elevated renal vascular resistance (RVR) of a model of hypertension (e.g., SHR) can be corrected by a therapy directed at scavenging of intra-cellular and extra-cellular $O_2^-$.

EXAMPLE 4

Materials and Methods. In Example 4, the MAP during constant intravenous infusion of Tempol was compared in anesthetized SHR and WKY. To determine the dose-response relationship for Tempol, MAP was measured during basal conditions and during intravenous infusion of Tempol at 1.8, 18, 180, and 1800 μmol·kg$^{-1}$·h$^{-1}$ for 30 minutes in anesthetized WKY (n=6) and SHR (n=6).

Figure 2:
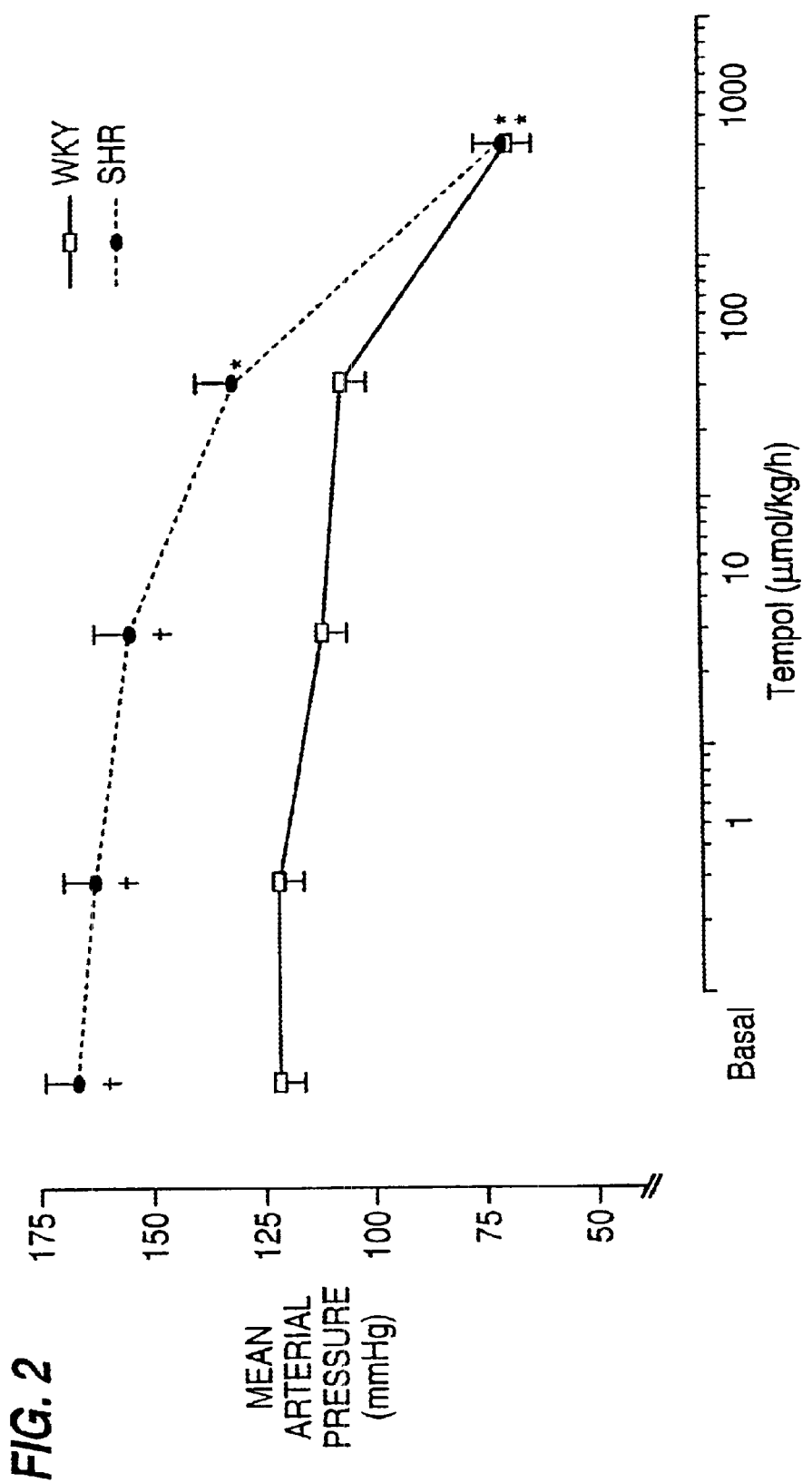
FIG. 2. MAP during baseline conditions (Basal) and during intravenous (i.v.) infusion of Tempol (1.8, 18, 180 and 1,800 $\mu$mol·kg$^{-1}$·h$^{-1}$) in anesthetized WKY (□, =6) and SHR (●, n=6). *P<0.05 vs. Basal; †P<0.05 vs. WKY.
Figure 3:
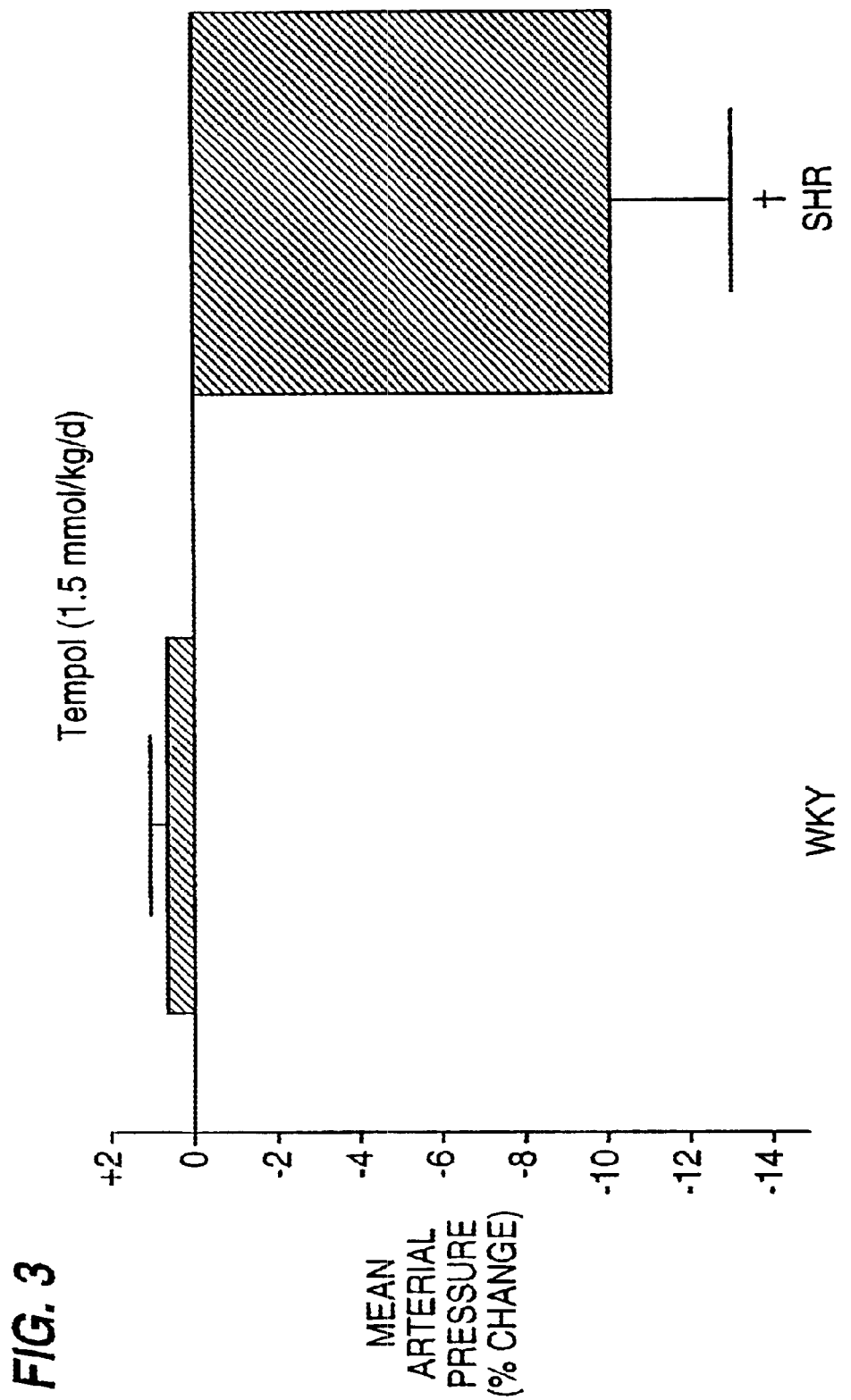
FIG. 3. Percent change in MAP after 7 days of Tempol administration (1.5 mmol·kg$^{-1}$·h$^{-1}$ i.p.) in WKY (n=7) and SHR (n=7). †P<0.05 vs. WKY.

FIG. 2 illustrates the dose-response relationship between Tempol at 1.8, 18, 180, 1,800 μmol·kg$^{-1}$·h$^{-1}$ and MAP in WKY and SHR. Baseline MAP was again significantly (P<0.05) elevated in the SHR (166±7 mm Hg) compared with WKY (121±4 mm Hg). Tempol dose-dependently decreased MAP in WKY and SHR, with SHR having a greater sensitivity and responsiveness to Tempol infusion. The highest dose of Tempol (1,800 μmol·kg$^{-1}$·h$^{-1}$) normalized the MAP of SHR (72±10 mm Hg) to the level of WKY (71±3 mm Hg).

EXAMPLE 5

Materials and Methods. In Example 5, the role of NO in the MAP response to constant Tempol infusion in SHR was investigated To determine whether $O_2^-$ increases MAP through interaction with the NO pathway, the MAP response to Tempol was determined in anesthetized SHR (n=6) and in SHR pretreated with the NO synthase inhibitor L-NAME (11 μmol·kg$^{-1}$·min$^{-1}$, n=5). To ensure that any change in the MAP response to Tempol in SHR during L-NAME administration was not due solely to an increase in MAP and vascular tone, the protocol was repeated in SHR infused with norepinephrine (31 μmol·kg$^{-1}$·min$^{-1}$, n=6). In all rats, MAP was measured during basal conditions; during 20 minutes of pretreatment with either saline vehicle, L-NAME, or norepinephrine; and after 30 minutes of constant Tempol infusion (180 μmol·kg$^{-1}$·h$^{-1}$).

Results. The percent change in MAP was compared in SHR pretreated with isotonic saline vehicle (2 mL/h i.v.) or the NO synthesis inhibitor L-NAME (11 μmol·kg$^{-1}$·h$^{-1}$ i.v.). As in the previous group, infusion of Tempol (180 μmol·kg$^{-1}$·min$^{-1}$) for 30 minutes significantly decreased MAP by 32% in SHR (121±17 mm Hg, P<0.05). In marked contrast, the NO synthesis inhibitor L-NAME abolished the MAP response to Tempol. Twenty minutes of L-NAME infusion alone increased MAP by 18% from 158±11 to 187±8 mm Hg, and MAP remained unchanged during Tempol infusion (186±4 mm Hg). Time control studies in a separate group of SHR showed that MAP remained steady during L-NAME infusion (change in MAP at 50 min, 0.3±3.3%; NS).

To investigate whether the failure of Tempol to lower MAP in L-NAME-infused rats was a consequence of the severe vasoconstriction and hypertension, the protocol was repeated in SHR infused with norepinephrine (31 nmol·kg$^{-1}$·min$^{-1}$) in place of L-NAME. Norepinephrine increased MAP by 15% from 164±4 to 188±7 mm Hg. This was similar to the increase with L-NAME. However, Tempol significantly decreased MAP by 14% (161±7 mm Hg, P<0.05) in SHR infused with norepinephrine. Time-control studies, in a separate group of SHR, showed that MAP remained steady during norepinephrine infusion (change in MAP at 50 min, 2.0±0.0%; NS).

Therefore, this example shows that the antihypertensive response must depend on NOS, because it was blocked by NO synthesis inhibition. The intravenous infusion of Tempol decreases MAP by 32% in SHR, and this response is blocked in SHR rats pretreated with the NO synthase inhibitor L-NAME. It has also been shown that the negative response to Tempol during L-NAME was not merely due to an increase in systemic vascular resistance and blood pressure, because of the MAP response to TEMPOL in SHR infused with norepinephrine. In SHR pretreated with norepinephrine, which produced a similar increase in MAP, Tempol reduced MAP by 14%. Previous investigators have shown that catecholamines, including norepinephrine, have antioxidant properties. Because norepinephrine is an antioxidant, the addition of another antioxidant would not have as marked an effect as Tempol administered alone to rats. For this reason, Tempol may have been less effective in lowering MAP in SHR pretreated with norepinephrine (14%) than in normal SHR (32%). Overall, these data suggest that NO plays an important role in mediating the antihypertensive actions of scavenging of $O_2^-$.

There are several possible mechanisms that should be considered by which NO mediates the antihypertensive actions of Tempol. First, could Tempol directly donate NO? This possible mechanism has been proven incorrect, because Tempol does not decompose to NO (Landino et al., 1996 *Proc. Natl Acad. Sci. USA* 93: 15069–15074). Second, scavenging of $O_2^-$ increases the half-life of NO. Gryglewski et al. (1986 *Nature* 320: 454–456) showed that $O_2^-$ is important in the breakdown of NO to peroxynitrite, and Rubanyi et al. (1986) demonstrated that $O_2^-$ inactivates NO in coronary artery rings. There are several possible sources of $O_2^-$, including xanthine oxidase, NADPH oxidase, incomplete electron transport and even brain NOS (Samuni et al., 1991 *Clin. Invest.* 1526–1530). The source of $O_2^-$ in this study remains unclear. However, because previous studies suggest a role of $O_2^-$ released from the vasculature in SHR, brain NOS does not appear to be the major source of $O_2^-$. As a result of the powerful interaction between $O_2^-$ and NO, Tempol may prolong the half-life of NO and thus allow it to exert a more powerful vasodilatory action. Finally, by blocking the formation of peroxynitrite, Tempol may inhibit the production of vasoconstrictor endoperoxides that are stimulated by peroxynitrite in macrophages (Landino et al., 1996). Nevertheless, this is the first study to show that scavenging of $O_2^-$ both extracellularly and intracellularly with a membrane permeable SOD mimetic, such as Tempol, normalizes the RVR and MAP of SHR. Other SOD nitroxide mimetics are also considered (see Schnackenberg et al., 1998).

EXAMPLE 7

Materials and Methods. Groups of male SHR and WKY rats (250±10 g) were maintained on tap water and a standard chow (Ralston-Purina Co., sodium content 0.3 g/100 g). Rats were divided into four groups: WKY given vehicle (n=7), SHR given vehicle (n=8), WKY given Tempol (n=6), and SHR given Tempol (n=8). Tempol is readily soluble in water and was administered in the drinking water (1 mM) for two weeks. After either control or Tempol administration, rats were maintained in metabolic cages for 24 hours. Urine was collected in containers with 10 μl of 2 mM ethylenediaminetetraacetic acid (EDTA) to prevent ex vivo production of 8-iso-prostaglandin $F_{2\alpha}$ (8-ISO). Urine was centrifuged at 1,000 rpm for 10 min at 4° C. and stored in aliquots at −80° C. until assayed.

Thereafter, WKY and SHR were anesthetized with thiobutabarbital (100 mg/kg, i.p., Inactin, Research Biochemicals International) and maintained at 37° C. on a servo-controlled heated rodent operating table. A tracheostomy was performed with polyethylene PE-240 tubing and the left jugular vein and carotid artery were cannulated with PE-50 tubing. A 1% albumin solution in 0.154 M NaCl was infused at 2 ml/h, i.v. to maintain a euvolemic state. A midline incision was made and the left renal artery was isolated. A blood flow probe was placed around the renal artery and connected to a transit-time blood flowmeter (IRB, Transonic Systems, Inc.). We have previously shown that this method of measuring real-time changes in renal blood flow (RBF) is valid in the rat. Mean arterial pressure (MAP) and heart rate (HR) were continuously recorded from the carotid artery using a Statham pressure transducer (model P23, Gould Instruments) and MACLab data acquisition software. Glomerular filtration rate (GFR) was determined from the clearance of [$^3$H]-inulin. Following surgery and a 60 min equilibration period, MAP, HR, GFR, and RBF were measured over 30 minutes and the data was averaged.

Statistics. All values shown are mean±SE. ANOVA was used to determine statistical significance in groups 1 and 2. Student's t test was used to determine significance in groups 3 and 4, where the comparison was limited to two observations. $P < 0.05$ was considered statistically significant.

Results. Rats maintained on Tempol given in the drinking water for 2 weeks had similar dietary consumption as control rats drinking water alone. There was no significant difference between food intake (Control: 25±1 vs. Tempol: 24±1 g/day) or body weight gain (Control: 69±4 vs. Tempol: 66±3 g/14 days), but water intake was increased modestly in the Tempol treated groups (Control: 34±2 vs. Tempol: 43±3 ml/day, p<0.05). Water intake was increased similarly in Tempol-treated WKY and SHR.

Figure 4:
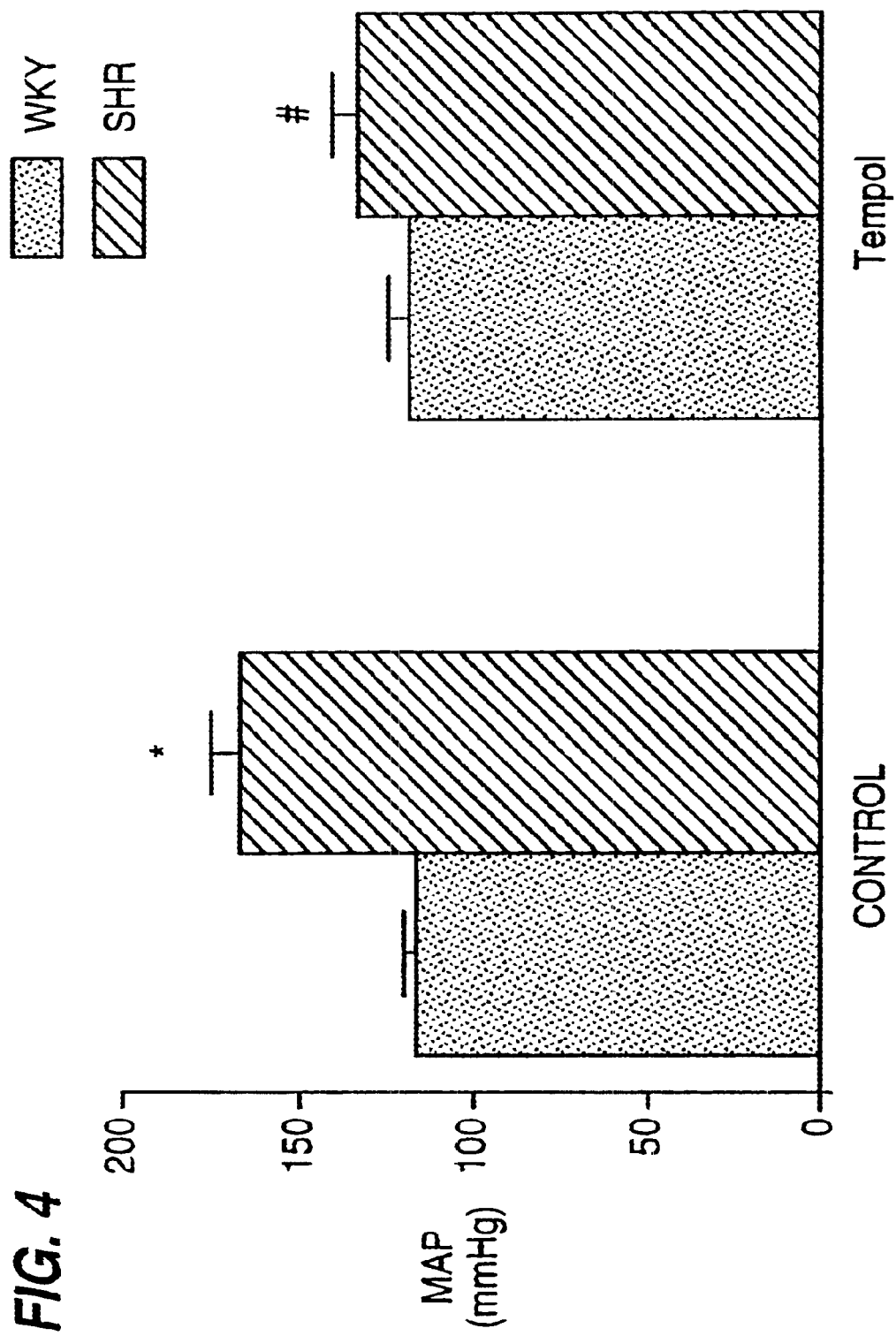
FIG. 4. Mean arterial pressure (MAP) in WKY and SHR during control conditions (Control) and after two weeks of oral Tempol treatment (1 mM, Tempol, added to the drinking water). *p<0.05 vs. WKY. #p<0.05 vs. Control.

Mean arterial pressure in WKY and SHR is represented in FIG. 4. Under normal conditions, MAP in SHR was increased by 41% compared to WKY (SHR: 162±8 vs. WKY: 115±5 mm Hg, p<0.001). After two weeks of Tempol administration, MAP was reduced in SHR to a value that was not significantly different from WKY (SHR: 134±6 vs. WKY: 118±7 mm Hg). MAP in SHR given Tempol was significantly lower by 18% compared to normal SHR. Analysis of variance showed that Tempol specifically and significantly (p<0.05) decreased MAP in SHR. Heart rate was significantly (p<0.001) elevated in SHR (420±6 bts/min) compared to WKY (374±9 bts/min) during control conditions and was not changed by Tempol (SHR: 414±9 vs. WKY: 373±8 bts/min). Two weeks of Tempol administration in the drinking water (1 mM) to SHR (n=8) decreased MAP by 18% (162±8 to 134±6 mm Hg, p<0.05), increased GFR by 17% (1.6±0.2 to 1.9±0.3 ml/min) and decreased UV8-ISO by 39% (9.8±0.7 to 6.0±0.7 ng/24 hr, p<0.05).

TABLE 5

| Group | RBF ml/min | GFR ml/min | RVR mm Hg/ml/min | UV ml/24 hr | $U_{Na}V$ mmol/24 hr |
|---|---|---|---|---|---|
| Control WKY | 8.8 ± 0.7 | 3.0 ± 0.4 | 13.5 ± 1.0 | 14.2 ± 1.5 | 2.6 ± 0.3 |
| Control SHR | 5.8 ± 0.6* | 1.6 ± 0.2* | 29.4 ± 2.7* | 13.8 ± 2.2 | 2.0 ± 0.3 |

TABLE 5-continued

| Group | RBF ml/min | GFR ml/min | RVR mm Hg/ml/min | UV ml/24 hr | $U_{Na}V$ mmol/24 hr |
|---|---|---|---|---|---|
| Tempol WKY | 8.8 ± 0.9 | 2.5 ± 0.4 | 14.2 ± 1.4 | 16.7 ± 2.3 | 2.4 ± 0.6 |
| Tempol SHR | 5.6 ± 0.5* | 2.0 ± 0.2 | 26.4 ± 2.6* | 15.2 ± 1.7 | 2.1 ± 0.2 |

Table 5 depicts renal hemodynamic and excretory function during normal conditions and after 2 weeks of Tempol administration in the drinking water. Under normal conditions, the RBF of SHR was decreased by 34% (SHR: 5.8±0.6 vs. WKY: 8.8±0.7 ml/min, p<0.01), the GFR was decreased by 47% (SHR: 1.6±0.2 vs. WKY: 3.0±0.4 ml/min, p<0.05), and the RVR was increased by 117% (SHR: 29.4±2.7 vs. WKY: 13.5±1.0 mm Hg/ml/min, p<0.001). After two weeks of Tempol administration, there were no significant changes in renal hemodynamics in SHR, although there were tendencies towards a decrease in RVR (16%) and an increase in GFR (17%), such that there was no longer a significant difference in GFR between SHR and WKY. Tempol had no marked effects on renal hemodynamics in WKY. Renal excretory function was not significantly different between WKY and SHR during control conditions or Tempol administration.

This example demonstrates that prolonged oral Tempol therapy selectively lowers the BP in a rat model of essential hypertension, but without effect on the WKY control rats. Importantly, the marker of $O_2^-$ generation (e.g., excretion of 8-ISO) was increased in the SHR model, yet Tempol selectively reduced this marker to the value observed in the WKY control rats over the two week period of its administration. This is the first demonstration that steady-state administration of an agent (e.g., Tempol) can simultaneously and selectively correct hypertension and oxidative stress in a model of human essential hypertension. It provides a strong, rational basis for these forms of therapy in human essential hypertension.

Increased ROS was detected in our study of the rat model of mild/moderate essential hypertension (e.g., the SHR rat). It is likely that the ROS is more severe and ROS reversal is more important and urgent in the more severe forms of hypertension, such as accelerated, drug-resistant or malignant hypertension, or hypertensive urgencies, emergencies and crises. Therefore, the more severe forms of hypertension, that are often accompanied by dysfunction of the heart or brain, may be the forms of hypertension best treated by Tempol containing compositions.

In the above setting, patients often require intravenous therapy in a hospital under close monitoring in an intensive care unit. The drug of choice currently is usually the NO donor compound sodium nitroprusside (Nipride). Our data demonstrates that Tempol acts synergistically with S-nitrosopenacillamine (SNAP) in our rat studies to reduce glomerular capillary pressure by relaxing the efferent arteriole of the kidney. This provides a potential basis for combining Tempol with NO providing agents, such as Nipride, in certain patients.

Although the present invention has been described in detail with reference to examples above, it is understood that various modifications can be made without departing from the spirit of the invention. Accordingly, the invention is limited only by the following claims. All cited patents and publications referred to in this application are herein incorporated by reference in their entirety. This application also incorporates in its entirety patent application Ser. No. 08/933,379 filed Sep. 19, 1997.

I claim:

1. A method of treating hypertension, a hypertensive emergency, a hypertensive crisis or essential hypertension in a patient comprising the step of administering to said patient a blood pressure lowering effective amount of a nitroxide in a pharmaceutically acceptable carrier, wherein said nitroxide is selected from the group consisting of TEMPO, DOXYL and PROXYL.

2. The method of claim 1, wherein said nitroxide in a pharmaceutically acceptable carrier is administered orally.

3. The method of claim 1, wherein said nitroxide in a pharmaceutically acceptable carrier is administered parenterally.

4. The method of claim 1, wherein said nitroxide in a pharmaceutically acceptable carrier is administered intravenously.

5. The method of claim 1, wherein said nitroxide in a pharmaceutically acceptable carrier is administered transdermally.

6. A method of treating hypertension, a hypertensive emergency, a hypertensive crisis or essential hypertension comprising administering to a patient in need thereof a therapeutically effective amount of a pharmaceutical composition comprising Tempol, wherein said Tempol is formulated to deliver a bolus dose intravenously of about 0.025 mg/kg to about 400 mg/kg.

7. A method of treating hypertension, a hypertensive emergency, a hypertensive crisis or essential hypertension comprising administering to a patient in need thereof a therapeutically effective amount of a pharmaceutical composition comprising Tempol, wherein said Tempol is formulated to deliver a bolus dose intravenously of about 0.025 mg/kg to about 40 mg/kg.

8. A method of treating hypertension, a hypertensive emergency, a hypertensive crisis or essential hypertension comprising administering to a patient in need thereof a therapeutically effective amount of a pharmaceutical composition comprising Tempol, wherein said Tempol is formulated to deliver a bolus dose intravenously of about 0.25 mg/kg to about 4 mg/kg.

9. A method of treating hypertension, a hypertensive emergency, a hypertensive crisis or essential hypertension comprising administering to a patient in need thereof a therapeutically effective amount of a pharmaceutical composition comprising Tempol, wherein said Tempol is formulated to deliver an intravenous dose of about 0.05 mg/kg/hr to about 1000 mg/kg/hr by intravenous infusion.

10. A method of treating hypertension, a hypertensive emergency, a hypertensive crisis or essential hypertension comprising administering to a patient in need thereof a therapeutically effective amount of a pharmaceutical composition comprising Tempol, wherein said Tempol is formulated to deliver an intravenous dose of about 0.05 mg/kg/hr to about 100 mg/kg/hr by intravenous infusion.

11. A method of treating hypertension, a hypertensive emergency, a hypertensive crisis or essential hypertension comprising administering to a patient in need thereof a therapeutically effective amount of a pharmaceutical composition comprising Tempol, wherein said Tempol is formulated to deliver an intravenous dose of about 0.5 mg/kg/hr to about 10 mg/kg/hr by intravenous infusion.

12. A method of treating essential hypertension comprising administering to a patient in need thereof a therapeutically effective amount of a patch for dermal administration of Tempol wherein said Tempol is formulated to provide about 200 mg per square centimeter of said patch.

13. A method of treating hypertension, a hypertensive emergency, a hypertensive crisis or essential hypertension comprising the step of administering to a subject in need thereof an effective amount of a pharmaceutical composition comprising Tempo, Tempol, Doxyl or Proxyl, wherein said Tempo, Tempol, Doxyl or Proxyl is formulated to deliver an oral daily dose of about 0.07 mg/kg/day to about 7500 mg/kg/day.

14. The method of claim 13, wherein said Tempo, Tempol, Doxyl or Proxyl is formulated to deliver an oral daily dose of about 0.07 mg/kg/day to about 750 mg/kg/day.

15. The method of claim 14, wherein said Tempo, Tempol, Doxyl or Proxyl is formulated to deliver an oral daily dose of about 0.7 mg/kg/day to about 75 mg/kg/day.

16. A method of treating hypertension, a hypertensive emergency, a hypertensive crisis or essential hypertension comprising the step of administering to a subject in need thereof an effective amount of a pharmaceutical composition comprising Tempo, Tempol, Doxyl or Proxyl, wherein said Tempo, Tempol, Doxyl or Proxyl is formulated to deliver an intravenous bolus dose of about 0.025 mg/kg to about 400 mg/kg.

17. The method of claim 16, wherein said Tempo, Tempol, Doxyl or Proxyl is formulated to deliver an intravenous bolus dose of about 0.025 mg/kg to about 40 mg/kg.

18. The method of claim 17, wherein said Tempo, Tempol, Doxyl or Proxyl is formulated to deliver an intravenous bolus dose of about 0.25 mg/kg to about 4 mg/kg.

19. A method of treating hypertension, a hypertensive emergency, a hypertensive crisis or essential hypertension comprising the step of administering to a subject in need thereof an effective amount of a pharmaceutical composition comprising Tempo, Tempol, Doxyl or Proxyl, wherein said Tempo, Tempol, Doxyl or Proxyl is formulated to deliver a dose of about 0.05 mg/kg/hr to about 1000 mg/kg/hr by intravenous infusion.

20. The method of claim 19, wherein said Tempo, Tempol, Doxyl or Proxyl is formulated to deliver a dose of about 0.05 mg/kg/hr to about 100 mg/kg/hr by intravenous infusion.

21. The method of claim 20, wherein said Tempo, Tempol, Doxyl or Proxyl is formulated to deliver a dose of about 0.5 mg/kg/hr to about 10 mg/kg/hr by intravenous infusion.

22. A method of treating hypertension, a hypertensive emergency, a hypertensive crisis or essential hypertension comprising the step of administering to a subject in need thereof an effective amount of a pharmaceutical composition comprising Tempo, Tempol, Doxyl or Proxyl, wherein said Tempo, Tempol, Doxyl or Proxyl is formulated for delivery transdermally via a patch, wherein said Tempo, Tempol, Doxyl or Proxyl is present on said patch at a concentration of about 200 mg per square centimeter of said patch.

* * * * *